United States Patent [19]

Cook et al.

[11] Patent Number: 5,406,016
[45] Date of Patent: Apr. 11, 1995

[54] TRANSALKYLATION OF BENZENE WITH HEAVY CATALYTIC NAPHTHA

[75] Inventors: Bruce R. Cook; William E. Winter; Kenneth L. Riley, all of Baton Rouge, La.

[73] Assignee: Exxon Research and Engineering Company, Florham Park, N.J.

[21] Appl. No.: 73,026

[22] Filed: Jun. 7, 1993

[51] Int. Cl.⁶ .............................................. C07C 5/52
[52] U.S. Cl. ................................. 585/475; 585/323; 585/467; 208/62
[58] Field of Search ............... 585/467, 470, 475, 323; 208/62

[56] References Cited

U.S. PATENT DOCUMENTS

| | | | |
|---|---|---|---|
| 3,948,758 | 4/1976 | Bonacci et al. | 585/474 |
| 3,957,621 | 5/1976 | Bonacci et al. | 585/475 |
| 4,131,536 | 12/1978 | Adams et al. | 585/470 |
| 4,172,813 | 10/1979 | Feinstein et al. | 585/489 |
| 4,599,470 | 7/1986 | Gregory et al. | 585/323 |
| 4,950,823 | 8/1990 | Harandi et al. | 585/467 |
| 5,053,573 | 10/1991 | Jorgensen et al. | 585/467 |
| 5,082,983 | 1/1992 | Breckenridge et al. | 585/475 |

*Primary Examiner*—Anthony McFarlane
*Attorney, Agent, or Firm*—Henry E. Naylor

[57] ABSTRACT

A process for simultaneously converting benzene to predominantly methylbenzenes and reducing the concentration of $C_{10}+$ alkyl aromatics in a naphtha boiling range refinery process stream containing both benzene and $C_{10}+$ alkyl aromatics by contacting the stream at effective temperatures and pressures with a 12-ring zeolitic material.

15 Claims, No Drawings

TRANSALKYLATION OF BENZENE WITH HEAVY CATALYTIC NAPHTHA

FIELD OF THE INVENTION

The present invention relates to the transalkylation of benzene in a benzene containing stream with $C_{10}+$ alkyl aromatics from a stream containing said aromatics, which aromatics are characterized as being predominantly one ring compounds containing at least two $C_1-C_3$ alkyl groups. Predominantly methylbenzene is produced. The transalkylation reaction is catalyzed by a high silica to alumina 12-ring zeolitic material.

BACKGROUND OF THE INVENTION

The demand for cleaner transportation fuels is becoming greater every year. For example, there is great pressure in the United States, as well as in the European Community, for an ever cleaner gasoline pool. The gasoline pool is typically derived from several refinery processes, including gasoline from the catalytic cracking unit, straight run naphtha, reformate, and gasoline obtained as a low boiling by-product from various other refinery operations. Two of the major sources of gasoline are the reformer, in the form of a reformate, and the catalytic cracker, in the form of a heavy catalytic naphtha also referred to as heavy cat naphtha. Both sources present a problem meeting the terms of ever stricter environmental regulations. For example, reformate typically contains unacceptably high levels of benzene, and heavy catalytic naphtha typically contains unacceptably high levels of $C_{10}+$ aromatics.

Benzene is produced in a reformer by the dehydrogenation of $C_6$ cycloparaffins, the dehydrocyclization of straight chain paraffins of appropriate chain length ($C_6$), and dealkylation of other aromatics. In fact, most reforming units built in recent years are continuous catalytic reforming units which produce ever higher levels of benzene then do reforming units such as semi-regenerative and cyclic units.

While it is possible to remove benzene from the gasoline pool by fractionation techniques, such techniques are not preferred because the boiling point of benzene is too close to that of some of the more desirable organic components, $C_6$ paraffins and isoparaffins. Toluene and xylenes, are the more desirable organic components, as opposed to benzene, in gasoline because they are less objectionable from an environmental point of view.

Therefore, there is still a significant need in the art for methods of reducing the levels of benzene and $C_{10}+$ aromatics from refinery streams destined for the gasoline pool.

SUMMARY OF THE INVENTION

In accordance with the present invention, there is provided a process for simultaneously converting benzene to predominantly methylbenzenes and reducing the concentration of $C_{10}+$ alkyl aromatics in a naphtha boiling range refinery process stream containing both benzene and $C_{10}+$ alkyl aromatics, which aromatics are characterized as being predominantly one ring compounds containing at least two alkly groups, which process comprises contacting said stream at a temperature from about 250° C. to 450° C. and a pressure with from about 400 to 2500 psig one or more 12-ring zeolitic materials having a silica to alumina mole ratio greater than or equal to 12.

In a preferred embodiment of the present invention, the zeolitic material is an ultra-stable Y zeolite or a zeolite beta.

In another preferred embodiment of the present invention, the $C_{10}+$ alkly aromatics are provided by a heavy catalytic naphtha refinery stream and the benzene is provided by a reformate stream.

DETAILED DESCRIPTION OF THE INVENTION

The concentration of benzene in a reformate and the concentration of $C_{10}+$ aromatics in a refinery stream, such as a heavy catalytic naphtha or a heavy reformate, are simultaneously reduced by the practice of the present invention, with the production of predominantly methylbenzenes. This is accomplished by blending a reformate stream with a $C_{10}+$ aromatic containing stream, then contacting this blended stream, at effective temperatures and pressures, with a 12-ring zeolitic material. Effective temperatures and pressures are those which will cause a transalkylation reaction of benzene to predominantly methylbenzene. By predominantly methylbenzene we mean that more methylbezene will be produced as opposed to any other benzene product. Such conditions will typically include a temperature in the range of about 250° C. to 450° C., preferably from about 275° C. to about 325° C. more preferably from about 275° C. to 300° C.; and pressures from about 400 psig to 2500 psig, preferably from about 800 to 1500 psig, and a hydrogen treat rate of about 100 to 6000 standard cubic feet per barrel (SCF/B), preferably from about 200 to 2000 SCF/B.

Any refinery reformate stream is suitable for use in the practice of the present invention, as long as it contains a level of benzene that needs to be reduced. A reformate stream will typically contain from about 5 to 60 mole % benzene, more typically from about 20 to 30 mole %, particularly reformate streams produced from the reaction of a platinum-containing supported catalyst. Reformate streams usually contain $C_6$ to $C_8$ aromatic hydrocarbons and $C_5$ to $C_6$ non-aromatic hydrocarbons, with the aromatic hydrocarbons being contributed mainly by benzene, toluene, xylene, and ethylbenzene.

Any suitable stream which contains $C_{10}+$ alkyl aromatics which are predominantly one ring compounds having two or more $C_1-C_3$ alkyl groups may be used in the practice of the present invention. It is preferred that the alkyl groups be methyl groups. A preferred stream containing such compounds is a heavy catalytic naphtha stream. Heavy catalytic naphtha streams will typically have a final boiling point in excess of about 200° C. to about 230° C., and contain from about 15 to 90 wt. %, preferably from about 15 to 50 wt. % of $C_{10}+$ aromatics. The $C_{10}+$ aromatics fraction will preferably be comprised of compounds having one ring wherein at least one of the alkyl groups is a methyl group, more preferably wherein at least two of the alkyl groups are methyl groups. Heavy catalytic naphtha streams will also contain two ring aromatic compounds, which are particularly bad for meeting governmental emissions requirements.

Zeolitic materials suitable for use herein are the 12-ring zeolite catalytic materials, such as ultrastable Y zeolite, zeolite beta, zeolite X, zeolite Y, mordenite, and ECR zeolites. Preferred are ultra-stable zeolite Y, and zeolite beta. More preferred is zeolite beta. Such catalytic materials are well known in the art. For example, zeolite Y is described in U.S. Pat. No. 3,130,007 which is incorporated herein by reference. Ultra-stable Y (USY) zeolite is typically produced by reducing the lattice aluminum content of zeolite Y by steaming. ECR zeolite are described in U.S. Pat. Nos. 4,879,103 and 4,93 1,267, which are incorporated herein by reference. Zeolite beta has been described in U.S. Pat. No. 3,308,069 which is incorporated herein by reference. The framework of zeolite beta has been described by Higgins et al in ZEOLITES, 1988, Vol. 8, November, pages 446–452. Zeolite beta can be readily synthesized in modifications having silica to alumina ratios of 25 to 75. It consists of tetrahedral framework disordered along [001]. It can be characterized by three mutually intersecting 12-ring channel systems permitting adsorption of larger hydrocarbon molecules such as those which enter the channel system in zeolite Y. It is preferred that the zeolite materials also contain a metals component to prevent rapid catalyst deactivation, and to hydrogenate two ring aromatics to one ring aromatics. But, too high a concentration of metals leads to saturation of the one ring aromatics, which is undesirable.

The metals content will be comprised of at least one metal from Group VIII and at least one metal from Group VI of the Periodic Table of the Elements. Preferred Group VIII metals include Fe, Ni and Co, more preferably Co. Preferred Group VI metals include Mo and W, more preferably Mo. The amount of Group VIII metal will range from about 0.1 to 20 wt. %, preferably from about 0.1 to 5 wt. %, more preferably from about 0.2 to 2 wt. %, and most preferably 0.2 to 0.6 wt. % based on the oxides and on the total weight of the catalyst. The amount of Group VI metal content will range from about 0.5 to 20 wt. %, preferably about 0.5 to 10 wt. %, more preferably about 0.5 to 5 wt. %, and most preferably about 1 to 2 wt. %, also based on the oxides and the total weight of the catalyst. It is understood that the zeolitic material maybe used in undiluted form, or they maybe mixed and copelleted with other relatively less active catalysts, diluents or binders, such as alumina, silica gel, silica-alumina cogels, activated clays, and the like in proportions ranging between 5 and 90 wt. %. Any suitable technique can be used to incorporate the metals into the zeolitic material, such as the well known incipient wetness technique.

The following examples are presented for illustrative purposes and should not be taken as limiting the invention in any way.

Example 1

Transalkylation tests were conducted with a model feed and several zeolite containing catalysts. The model feed was composed of about 10 wt. % benzene and about 10 wt. % tetramethylbenzene with the balance of the feed being dodecane (n-$C_{12}$).

The catalysts used for these experiments were prepared as 70% zeolite in an alumina binder, using conventional techniques well known in the art. The catalysts were prepared as 1/16" extrudates. The finished extrudates were then crushed and screened to 14/35 mesh sized materials. 0.4 wt. % CoO and 1.4 wt. % $MoO_3$ were deposited on the 14/35 mesh sized particles by incipient wetness using cobalt nitrate and ammonium heptamolybdate respectively as the metal sources. The resulting catalysts were then air dried overnight, further dried for 2 hours at 127° C. using a forced air oven, and finally air calcined at 538° C. for 2 hours. The catalysts and their designation are set forth in Table I below.

TABLE I

| Catalyst | Zeolite Component | $S_i/Al_2O_3$ |
| --- | --- | --- |
| A | Ultra Stable Y Zeolite (USY) | 7.4 |
| B | ECR - 30 | 10 |
| C | ECR - 32 | 10 |
| D | Zeolite Beta | 31 |
| E | ZSM-5 | 33 |

Catalysts A, B, and C are preferred catalysts of this invention. Catalyst D is a more preferred catalyst of this invention, while catalyst E is not a catalyst of the invention.

The finished catalysts were tested for transalkylation activity in a ⅜" diameter, upflow, fixed bed reactor. The catalysts were pre-sulfided in the reactor by contacting the catalysts with flowing gaseous 10 wt. % hydrogen sulfide in hydrogen and slowly increasing the temperatures to 400° C. over a 48 hour period. The catalyst was then cooled to 300° C. The model feed described above, and flowing hydrogen gas, were then introduced at 300° C., 2.0 liquid hourly space velocity (LHSV), 800 psig reactor pressure, and 1600 standard cubic feet per barrel (SCF/B) hydrogen gas treat rate. Liquid products were collected and analyzed by gas chromatographic analysis.

As shown in the data in Table II below, only the 12 ring structures; Catalyst A (USY), Catalyst B (ECR-30), Catalyst C (ECR-32), and Catalyst D (zeolite beta) were able to catalyze transalkylation and simultaneously lower both benzene and tetramethylbenzene. Catalyst E (ZSM-5) was capable of lowering the level of benzene but it caused an undesirable increase in the amount of $C_{10}$ aromatics via an alkylation side-reaction involving benzene and dodecane. Of the 12 ring zeolites, zeolite beta is clearly superior to the other 12-ring faujasites in benzene conversion, while USY provides the greatest activity for tetramethylbenzene conversion. Clearly the zeolite beta catalyst is preferred in the case where large amounts of benzene needs to be converted, and the USY catalyst is preferred in the case were only a relatively small amount of benzene conversion is needed relative to $C_{10}$ reduction conversion.

The results of these experiments are shown in Table II below.

TABLE II

| Catalyst | A | B | C | D | E |
| --- | --- | --- | --- | --- | --- |
| Mole % Aromatics Hydrogenation | <1 | <1 | <1 | <1 | <1 |
| Mole % Benzene Reduction | 33 | 18 | 20 | 49 | 89 |
| Mole % $C_{10}$ Aromatics Reduction | 64 | 36 | 29 | 47 | -44 |
| Mole % Aromatics Conversion to $C_7$-$C_9$ Alkyl Benzene | 47 | 27 | 27 | 48 | 30 |

Example 2

Transalkylation pilot plant tests were conducted with a 50/50 feed mixture of heavy cat naphtha (HCN) and light reformate (Lt Reformate). Feed composition and properties were as follow:

| | |
| --- | --- |
| Benzene, wt. % | 9.2 |
| $C_7$-$C_9$ alkylbenzenes, wt. % | 16.6 |

| -continued | |
|---|---|
| C$_{10}$+ alkylbenzenes, wt. % | 10.8 |
| 2R Aromatics, wt. % | 9.3 |
| Total Aromatics, wt. % | 45.9 |
| Nitrogen, wppm | 70 |

Two catalyst systems were used for these tests. One was a catalyst generally used for hydrocracking and comprised of NiMo oxides on a support comprised of 20 wt. % USY zeolite and 80 wt. % alumina. This formulation provides both acid sites required for transalkylation and metals sites required for hydrogenating multiring aromatics. This catalysts is designated catalyst F and was formed as 1/16" extrudates. The other was a staged catalyst system with a bed of hydrotreating catalyst followed by a bed of hydrocracking catalyst. This was done to convert some of the organic nitrogen compounds to ammonia and to partially hydrogenate multiring aromatic compounds prior to contacting these raw feeds with zeolite containing catalyst. The hydrotreating catalyst is designated G and is comprised of NiMo oxides on an alumina support. This particular catalyst was in 1.3 mm quadrilobe form. The hydrocracking catalyst is designated H and is comprised of NiMo oxides on a 80 wt. % USY zeolite/20 wt. % alumina support. This catalyst was also formed as 1/16" extrudates. All catalysts were sulfided with a mixture of hydrogen and hydrogen sulfide for these experiments. Catalyst properties prior to sulfiding are shown in Table III below.

TABLE III

| Catalyst | F | H | G |
|---|---|---|---|
| NiO, wt. % | 6.0 | 3.4 | 4.0 |
| MoO$_3$, wt. % | 15.5 | 13.6 | 24.5 |
| P, wt. % | 2.2 | — | — |
| Surface Area, m$^2$/gm | 297 | 375 | 165 |
| Pore Volume, cm$^3$/gm | 0.34 | 0.32 | 0.38 |

These pilot plant tests were conducted at 800 psig, 1000 SCF/B hydrogen, 0.85 LHSV catalyst space velocity, and 275° C. Conversion and yields are shown in Table IV below.

TABLE IV

| | Catalyst | |
|---|---|---|
| Yields, Wt. % | F | G/H |
| Benzene | 5.5 | 3.4 |
| C$_7$-C$_9$ alkylbenzenes | 20.2 | 12.1 |
| C$_{10}$+ alkylbenzenes | 3.9 | 3.9 |
| 2R Aromatics | 1.7 | 1.9 |
| Total Aromatics | 31.3 | 21.3 |
| 190° C. Conversion, Wt. % | 33 | 32 |

With these catalyst systems, benzene, C$_{10}$+ alkyl benzenes and 2-ring aromatics were all reduced. Evidence of a hydrogenation reaction is found in the reduction of both single and two-ring aromatic compounds. Evidence of transalkylation reactions is found in a shift in aromatics distributions. More specifically, most of the aromatic compounds produced in these experiments were C$_7$, C$_8$, or C$_9$ alkylbenzenes. By way of contrast, most of the feed aromatic compounds were either benzene, C$_{10}$+ alkylbenzenes, or 2 ring aromatics. In fact, the hydrocracking catalyst system, F, produced additional C$_7$, C$_8$, and C$_9$ alkyl benzenes while reducing total aromatics levels indicating a high level of transalkylation activity.

Example 3

Additional transalkylation pilot plant tests were conducted with a 50/50 feed mixture of hydrotreated heavy cat naphtha and light reformate. Feed composition and properties were as follow:

| Benzene, wt. % | 8.9 |
|---|---|
| C$_7$-C$_9$ alkylbenzenes, wt. % | 25.5 |
| C$_{10}$+ alkylbenzenes, wt. % | 15.8 |
| 2R Aromatics, wt. % | 12.6 |
| Total Aromatics, wt. % | 62.8 |
| Nitrogen, wppm | <5 |

Four catalyst were used for these tests. The first was catalyst H described in Example 2 above. The others were Catalysts A, D, and E as described in Example 1 above. All catalysts used in these tests were in 1/16" extrudate form.

These tests were conducted at 600 psig, 1000 SCF/B hydrogen, and 0.85 LHSV catalysts space velocity. Two temperatures were used in these tests, 300° C. and 275° C. Conversions and yields for these experiments are shown in Table V below.

TABLE V

| | Catalyst | | | |
|---|---|---|---|---|
| Yields, Wt. % | H | A | D | E |
| Transalkylation of HCN/Lt Reformate at 275° C. | | | | |
| Benzene | 5.1 | 5.6 | 6.1 | 4.9 |
| C$_7$-C$_9$ alkylbenzenes | 31.3 | 24.7 | 35.2 | 27.7 |
| C$_{10}$+ alkylbenzenes | 9.7 | 12.4 | 12.9 | 16.4 |
| 2R Aromatics | 4.5 | 9.3 | 8.5 | 13.5 |
| Total Aromatics | 50.6 | 52.0 | 62.7 | 62.5 |
| 190° C. Conversion, Wt. % | 4 | −15 | 8 | −30 |
| Transalkylation of HCN/Lt Reformate at 300° C. | | | | |
| Benzene | 7.9 | 8.3 | 1.7 | 6.1 |
| C$_7$-C$_9$ alkylbenzenes | 26.4 | 23.2 | 60.7 | 24.8 |
| C$_{10}$+ alkylbenzenes | 9.8 | 10.8 | 0.0 | 12.2 |
| 2R Aromatics | 7.6 | 8.4 | 0.3 | 9.8 |
| Total Aromatics | 51.7 | 50.7 | 62.7 | 52.9 |
| 190° C. Conversion, Wt. % | 0 | 13 | 96 | 13 |

At 275° C., the three catalysts of this invention all reduced benzene, C$_{10}$+ alkylbenzenes and 2-ring aromatics. The most preferred, the zeolite beta containing catalyst, D, showed the best selectivity for transalkylation, producing the highest yield of C$_7$ through C$_9$ alkylbenzenes with little or no total aromatics reduction. The comparison catalyst, E, reduced benzene but did not reduce heavy aromatics levels. The USY zeolite containing catalysts, H and A, also reduced total aromatics levels. The higher metals catalyst H was particularly effective for reducing heavy aromatics levels, presumably because of its higher metals level. At these conditions, none of the catalysts were particularly effective for converting 190° C.+ material to lighter feed products. However, the comparison catalyst E, which contained ZSM-5, actually produced more 190° C. from lighter feed components. This indicates that this ZSM-5 containing catalyst reduced benzene and lighter aromatics levels by paraffins/benzene alkylation reactions.

Catalyst D, the most preferred catalyst of this invention, showed the highest transalkylation activity observed in these experiments at 300° C. Benzene, C$_{10}$+ alkylbenzenes, and 2-ring aromatics were reduced to very low levels. Highest yields of C$_7$, C$_8$, and C$_9$ alkyl benzenes were produced with little or no total aromatics reduction. Moreover, most 190° C.+ feed was converted to lighter products. Catalysts H and A showed some activity for benzene and heavy aromatics reduction, but were less effective at the higher temperature than at 300° C. The comparison catalyst, E, produced more heavy aromatics than the catalysts of this invention, showing little or no transalkylation activity.

What is claimed is:

1. A process for simultaneously converting benzenes to predominantly methylbenzenes and simultaneously reducing the concentration of $C_{10}+$ alkyl aromatics in a naphtha boiling range refinery process stream which contains both benzene and $C_{10}+$ alkyl aromatics, which aromatics are predominantly one ring compounds containing two or more $C_1$–$C_3$ alkyl groups, which process comprises contacting said stream at a temperature in the range of about 250° C. to 450° C., and a pressure of about 400 to 2500 psig, with a 12-ring zeolitic material.

2. The process of claim 1 wherein the zeolitic material is selected from the group consisting of ultra-stable Y zeolites, ECR zeolites, faujasites, and zeolite beta.

3. The process of claim 2 wherein the zeolitic material is zeolite beta.

4. The process of claim 1 wherein the benzene is provided by a reformate stream and the $C_{10}+$ alkyl aromatics stream is provided by a heavy catalytic naphtha stream.

5. The process of claim 1 wherein the temperature is in the range of about 275° C. to 325° C.

6. The process of claim 5 wherein the pressure is in the range of about 800 to 1500 psig.

7. The process of claim 6 wherein the zeolitic material is zeolite beta.

8. The process of claim 7 wherein the benzene is provided by a reformate stream and the $C_{10}+$ alkyl aromatics stream is provided by a heavy catalytic naphtha stream.

9. The process of claim 1 wherein the zeolite material includes from about 0.1 to 20 wt. % of at least one metal from Group VIII and from about 0.5 to 20 wt. % of at least one metal from Group VI of the Periodic Table of the Elements.

10. The process of claim 1 wherein the amount of Group VIII metal is from about 0.2 to 2 wt. % and the amount of Group VI metal is from about 0.5 to 5 wt. %.

11. The process of claim 10 wherein the zeolitic material is zeolite beta.

12. The process of claim 10 wherein the amount of Group VIII metal is from about 0.2 to 0.6 wt. %, and the amount of Group VI metal is from about 1 to 2 wt. %.

13. The process of claim 12 wherein the zeolite material is a zeolite beta.

14. The process of claim 13 wherein the temperature is from about 275° C. to 325° C. and the pressure is from about 800 to 1500 psig.

15. The process of claim 1 wherein the benzene is provided by a reformate stream and the $C_{10}+$ alkyl aromatics stream is provided by a heavy catalytic naphtha stream.

* * * * *